(12) United States Patent
Nishide (10) Patent No.: US 7,145,984 B2
(45) Date of Patent: Dec. 5, 2006

(54) X-RAY CT SYSTEM, INFORMATION PROCESSING METHOD, AND STORAGE MEDIUM

(75) Inventor: Akihiko Nishide, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 60 days.

(21) Appl. No.: 10/918,936

(22) Filed: Aug. 16, 2004

(65) Prior Publication Data

US 2005/0041772 A1 Feb. 24, 2005

(30) Foreign Application Priority Data

Aug. 20, 2003 (JP) ............................. 2003-296293

(51) Int. Cl.
*H05G 1/64* (2006.01)
(52) U.S. Cl. ..................... 378/98.5; 378/165; 378/4; 378/901
(58) Field of Classification Search ............... 378/98.5, 378/165, 4–19, 108–117, 901
See application file for complete search history.

(56) References Cited

U.S. PATENT DOCUMENTS

| 3,679,902 A | * | 7/1972 | Hurst et al. ................... 378/97 |
| 4,160,906 A | | 7/1979 | Daniels et al. |
| 4,945,476 A | | 7/1990 | Bodick et al. |
| 5,233,519 A | | 8/1993 | Ito |
| 5,588,036 A | | 12/1996 | Fujise et al. |
| 5,807,256 A | | 9/1998 | Taguchi et al. |
| 6,424,692 B1 | * | 7/2002 | Suzuki ......................... 378/4 |
| 6,501,819 B1 | | 12/2002 | Unger et al. |
| 6,542,579 B1 | * | 4/2003 | Takasawa .................... 378/165 |
| 6,901,129 B1 | * | 5/2005 | Tachizaki et al. ............... 378/4 |
| 2004/0131139 A1 | * | 7/2004 | Oota et al. ..................... 378/4 |

FOREIGN PATENT DOCUMENTS

JP 09-299360 11/1997

* cited by examiner

*Primary Examiner*—Edward J. Glick
*Assistant Examiner*—Jurie Yun
(74) *Attorney, Agent, or Firm*—Armstrong Teasdale LLP (57) ABSTRACT

A method to plan a scan in consideration of past patient exposures. The method includes a step of sampling information on a patient exposure the subject has received during a scan performed for reconstructing tomographic images, which is appended to each of the reconstructed tomographic images, on the basis of identification information with which the subject is identified; a step of creating a distribution of patient exposures calculated relative to an axis orthogonal to the scanning directions on the basis of the sampled information on the patient exposure (an estimated patient exposure, which is estimated in planning a scan, and an exposure limit); and a step of displaying the created exposure distribution.

20 Claims, 11 Drawing Sheets

X-RAY CT SYSTEM, INFORMATION PROCESSING METHOD, AND STORAGE MEDIUM

CROSS REFERENCE TO RELATED APPLICATIONS

This application claims the benefit of Japanese Application No. 2003-296293 filed Aug. 20, 2003.

BACKGROUND OF THE INVENTION

The present invention relates to an X-ray computed tomography (CT) system that constructs tomographic images of a subject through X-irradiation.

In X-ray CT systems, an X-ray generation source that generates X-rays rotates about a subject (patient), and an X-ray detector detects X-rays transmitted by the patient at different angles of projection (this sequence is generally called a scan). The results of the scan are computerized in an operator console, whereby an image (X-ray tomographic image) of a section of the patient containing a region to be imaged (a plane at a sliced position, that is, a slice plane) is produced (reconstructed).

Normally, for the scan, an operator plans to determine the conditions for a scan or the conditions for reconstruction according to a region to be imaged or a purpose of diagnosis. The planning is called scan planning. The X-ray CT system generally includes a user interface helpful for scan planning.

When determining the conditions for a scan, an operator must take account of a patient exposure. The patient exposure can be calculated based on the settings of the conditions for a scan (for example, a tube current, a tube voltage, and a scan time). (An estimated patient exposure to be calculated based on the settings of the conditions for a scan shall be called a CTDI value.) Normally, the X-ray CT system has a facility for indicating the CTDI value through the user interface. The operator can therefore plan a scan at the sight of the CTDI value.

Moreover, some X-ray CT systems have a facility for retrieving the conditions for a scan determined in the past for a patient to be scanned (the conditions for a scan determined in consideration of an exposure in the past) from a database (refer to, for example, Patent Document 1). Using the facility, an operator can readily determine the conditions for a scan permitting high image quality while suppressing a patient exposure.

[Patent Document 1] Japanese Unexamined Patent Application Publication No. 9(1997)-299360

However, the conditions for a scan to be determined during scan planning are determined in consideration of an exposure a patient receives during a scan. No consideration is taken into a cumulative exposure representing the sum total of exposures the patient has received in the past during scans. However, if a patient does not recover for a long period of time, the patient may have the same region thereof radiographed a plurality of times during a certain period of time. In this case, even if a patient exposure per radiography is set to a value equal to or smaller than a reference value, the cumulative exposure the patient has received for the certain period of time may exceed the reference value.

In particular, a reference value permissible for a certain a patient's region to be imaged is small (for example, an exposure the eyeballs of the head receive during a certain period of time must be made lower than the exposures of the other regions). When the region including such a part is radiographed, a scan must be planned in consideration of an exposure per scan and a cumulative exposure as well. However, it is hard for the existing X-ray CT systems to plan a scan in consideration of the exposure per scan and cumulative exposure.

SUMMARY OF THE INVENTION

Therefore, an object of the present invention is to provide an X-ray CT system making it possible to readily plan a scan in consideration of a cumulative exposure of past exposures.

In order to solve the problem, an X-ray CT system in accordance with the present invention is provided with components described below.

An X-ray CT system for performing a scan so as to irradiate X-rays, which are generated from an X-ray tube, to a subject from a plurality of directions, and for reconstructing tomographic images of the subject, comprises: a holding means for holding information on an exposure a subject has received during a scan for image reconstruction while appending the information to each of the tomographic images; a creating means for sampling information on an exposure, which is held in the holding means, according to identification information with which the subject is identified, and for creating a distribution of exposures calculated relative to an axis orthogonal to the scanning directions; and a display means on which the created exposure distribution is displayed.

According to the present invention, a scan can be planned in consideration of past exposures.

Further objects and advantages of the present invention will be apparent from the following description of the preferred embodiments of the invention as illustrated in the accompanying drawings.

DETAILED DESCRIPTION OF THE INVENTION

A plurality of preferred embodiments of the present invention will be described in conjunction with drawings below. The same reference numerals are assigned to identical or equivalent components shown in the drawings.

[First Embodiment]

<Overall System Configuration>

Figure 1:
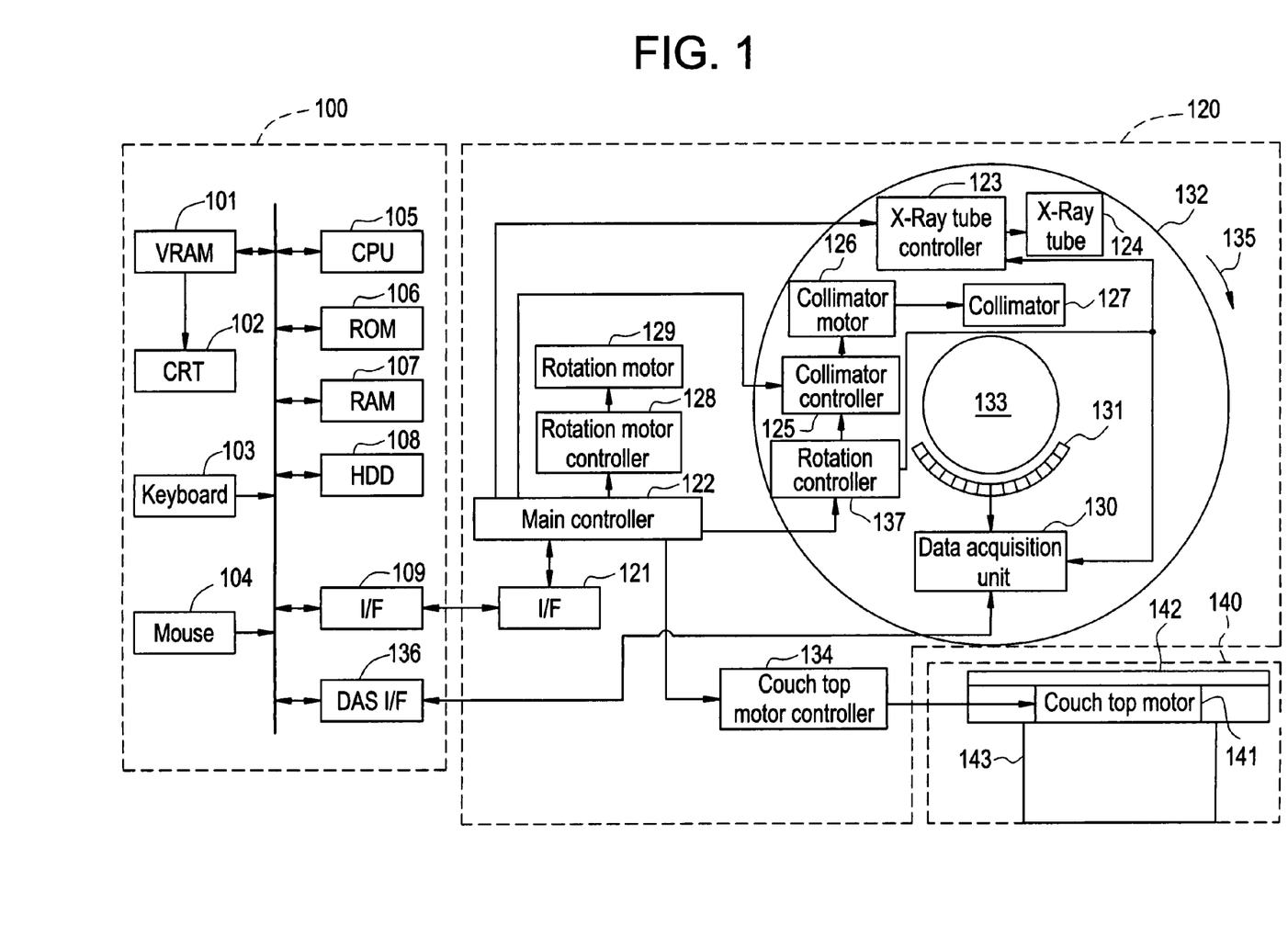
FIG. 1 is the overall system configuration of an X-ray CT system in accordance with a first embodiment of the present invention.

FIG. 1 shows the system configuration of an X-ray CT system in accordance with a first embodiment of the present invention.

As shown in FIG. 1, an X-ray CT system comprises: a gantry 120 that irradiates X-rays to a subject (patient) and detects X-rays transmitted by the subject lying down on a couch top; an operator console 100 that transmits a directive signal to the gantry 120 so as to determine various settings, reconstructs X-ray tomographic images on the basis of projection data sent from the gantry 120, and displays the images; and a transportation assembly 140 on which the subject lies down and which transports the subject to the inside of the gantry. According to the present embodiment, the subject refers to a "patient" (the same applies hereinafter). Moreover, a signal representing a directive to be given from the operator console 100 to the gantry 120 shall be called a "directive signal," and a signal used to control the internal components of the gantry 120 shall be called a "control signal" (the same applies hereinafter).

The gantry 120 has a main controller 122, which controls the entire gantry, and other components described below.

Reference numeral 121 denotes an interface through which the gantry 120 communicates with the operator console 100. Moreover, reference numeral 132 denotes a gantry rotary assembly in which an X-ray tube 124 that generates X-rays, a collimator 127 that defines a range of X-irradiation, a collimator motor 126 that is used to adjust the width of a slit of the collimator 127 defining the range of X-irradiation and to adjust the width in a Z-axis direction of the slit of the collimator 127 are incorporated. Incidentally, the z-axis direction refers to a direction perpendicular to the drawing, that is, a direction in which the couch top 142 is transported to a bore 133 and which is orthogonal to the scanning directions. A collimator controller 125 drives the collimator motor 126, and an X-ray tube controller 123 controls the X-ray tube 124.

Moreover, the gantry rotary assembly 132 comprises an X-ray detection unit 131 that detects X-rays transmitted by a subject, and a data acquisition unit 130 that acquires projection data detected by the X-ray detection unit 131. The X-ray detection unit 131 has a plurality of detector arrays, each of which includes a group of detection elements or a plurality of detection elements (channels), arranged in the Z-axis direction.

The X-ray tube 124 and collimator 127 are opposed to the X-ray detection unit 131 with the bore 133 interposed therebetween. With the positional relationship maintained, the gantry rotary assembly 132 rotates in a direction of arrow 135. The rotation is enabled by a rotation motor 129 whose rotating speed is controlled in predetermined control cycles in response to a driving signal sent from a rotation motor controller 128.

Moreover, the transportation assembly 140 includes the couch top 142 on which a subject actually lies down, and a patient couch 143 holding the couch top 142. The couch top 142 is driven in the Z-axis direction by means of a couch top motor 141. A transporting speed at which the couch top motor 141 is driven is controlled in predetermined control cycles according to a driving signal sent from a couch top motor controller 134.

The main controller 122 analyzes various directive signals received from the operator console 100 via the interface 121. Based on the results of the analysis, the X-ray tube controller 123, collimator controller 125, and data acquisition unit 130 output various control signals via a rotation controller 137, and transmit the various control signals to the rotation motor controller 128 and couch top motor controller 134. Moreover, projection data acquired by the data acquisition unit 130 is transmitted to the operator console 100 via a DAS interface 136.

The operator console 100 serves as a so-called workstation. As illustrated, the operator console 100 comprises a CPU 105 that is responsible for control of the entire system, a ROM 106 in which a boot loader and other programs are stored, a RAM 107 serving as a main memory, and other components described below.

An OS and a diagnostic program for organizing the entire X-ray CT system are stored in a hard disk drive (HDD) 108. Furthermore, past X-ray tomographic images of patients are stored in the HDD 108.

Moreover, a VRAM 101 is a memory in which image data representing an image to be displayed (mainly, 512 by 512 pixels) is developed. By developing image data in the VRAM 101, X-ray tomographic images can be displayed on a CRT 102. Reference numerals 103 and 104 denote a keyboard and a mouse that are used to enter various settings. Moreover, reference numeral 109 denotes an interface via which the operator console 100 communicates with the gantry 120.

As mentioned above, according to the present embodiment, past X-ray tomographic images of patients are stored in the HDD 108. The present invention is not limited to this mode. For example, the operator console 100 may be connected on an external network, and the past X-ray tomographic images may be stored in any data server on the network. In this case, the operator console 100 accesses the data server on the network if necessary, and retrieves any patient's past X-ray tomographic images from the database.

<Flow Ending With X-ray Tomographic Image Reconstruction>

The configuration of the X-ray CT system in accordance with the present embodiment is briefed above. A process of reconstructing an X-ray tomographic image using the X-ray CT system having the foregoing configuration is described in the flowchart of FIG. 2. The flowchart separately describes a process (a) to be executed in the operator console 100 and a process (b) to be executed in the gantry 120.

Figure 2A:
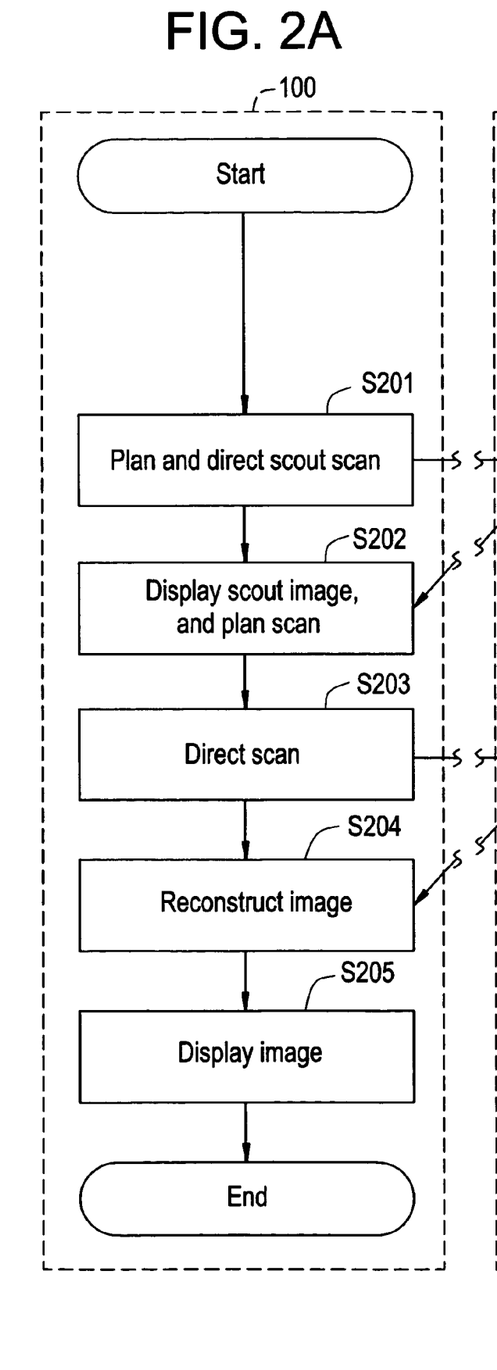
FIG. 2 concisely describes a flow ending with X-ray tomographic image reconstruction and being employed in a general X-ray CT system.
Figure 2B:
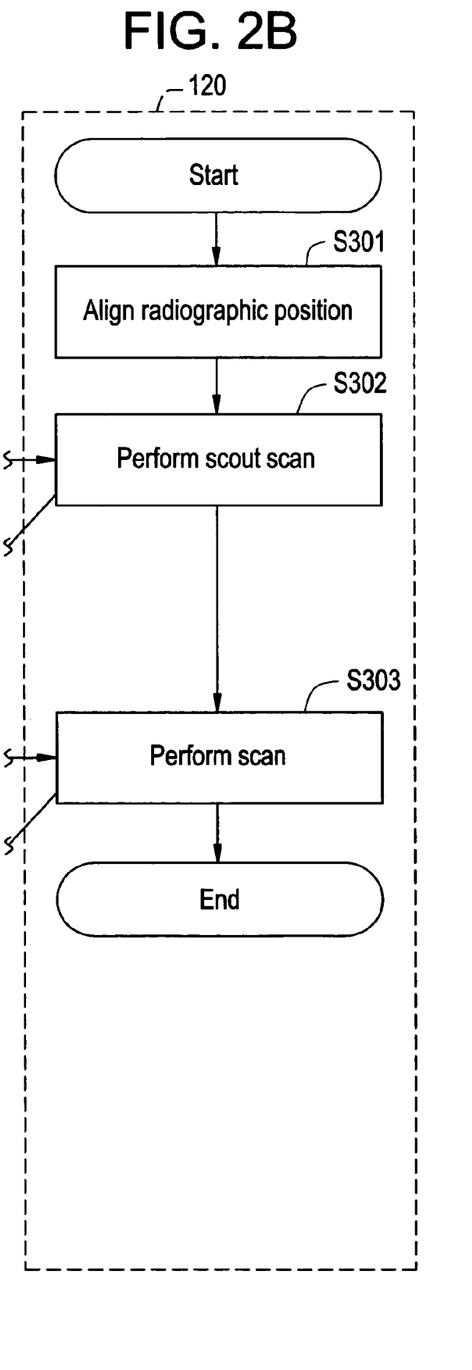

First, a patient is asked to lie down on the couch top 142. Alignment is performed for radiography (step S301). As soon as the alignment is completed, a scout scan is performed (step S302). The scout scan is such that the couch top 142 on which while the patient lies down is gradually transported with the X-ray tube 124 fixed at a predetermined position (that is, with the gantry rotary assembly 132 held intact at a certain angle of projection but not rotated), X-rays are continuously irradiated in order to acquire projection data (scanogram data) so as to construct one scanogram (scout image) of the patient.

Figure 3:
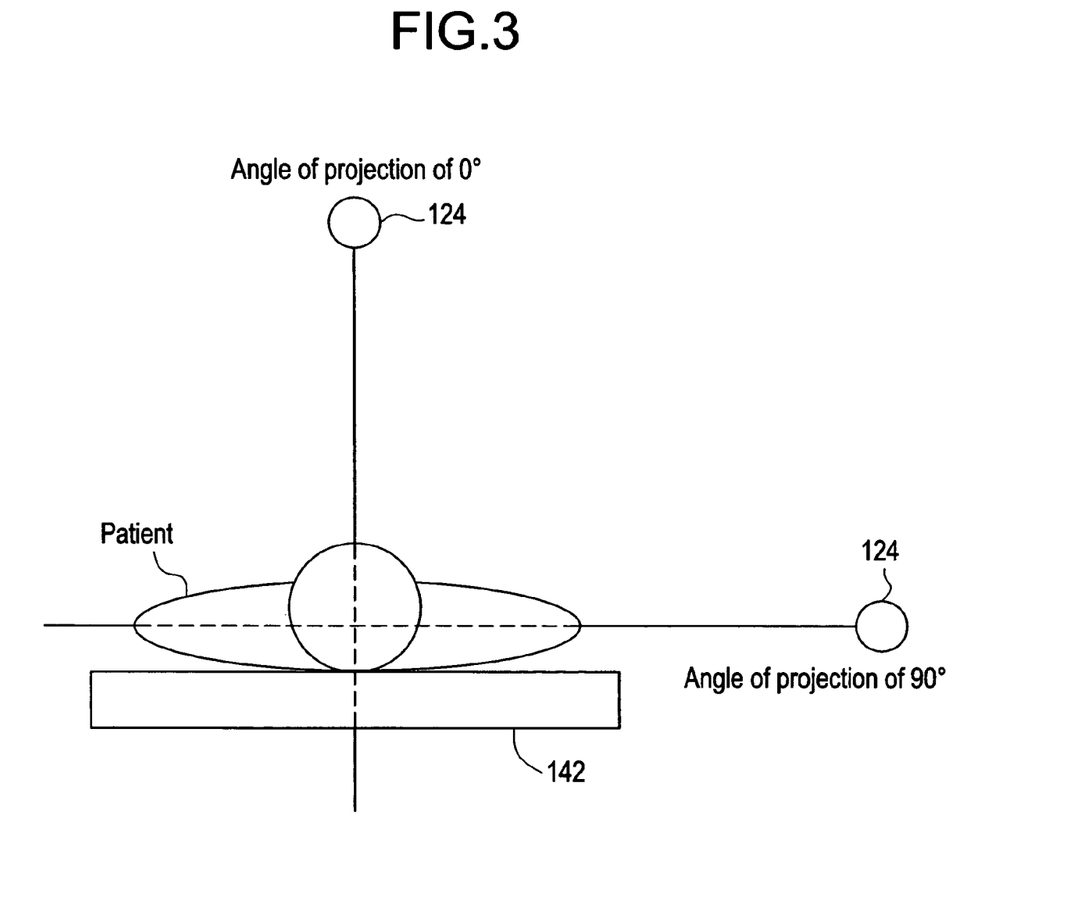
FIG. 3 is an explanatory diagram concerning a scout scan.

Herein, as shown in FIG. 3, the X-ray tube 124 is positioned at an angle of projection of 0° right above the patient, and a first scout scan is performed (under the control of the rotation motor controller 128). The X-ray tube 124 is, if necessary, positioned at an angle of projection of 90° right beside the patient, and a second scout scan is performed. Consequently, one or two kinds of scout images are constructed.

For a scout scan, first, the scout scan is planned at the operator console 100. Thereafter, an execution command is issued to the gantry 120 (step S201). A command that the conditions for a scout scan should be determined or a scout scan should be executed is issued through a setting screen image 400 (displayed on the CRT 102 of the operator console 100), for example, the one shown in FIG. 4.

Figure 4:
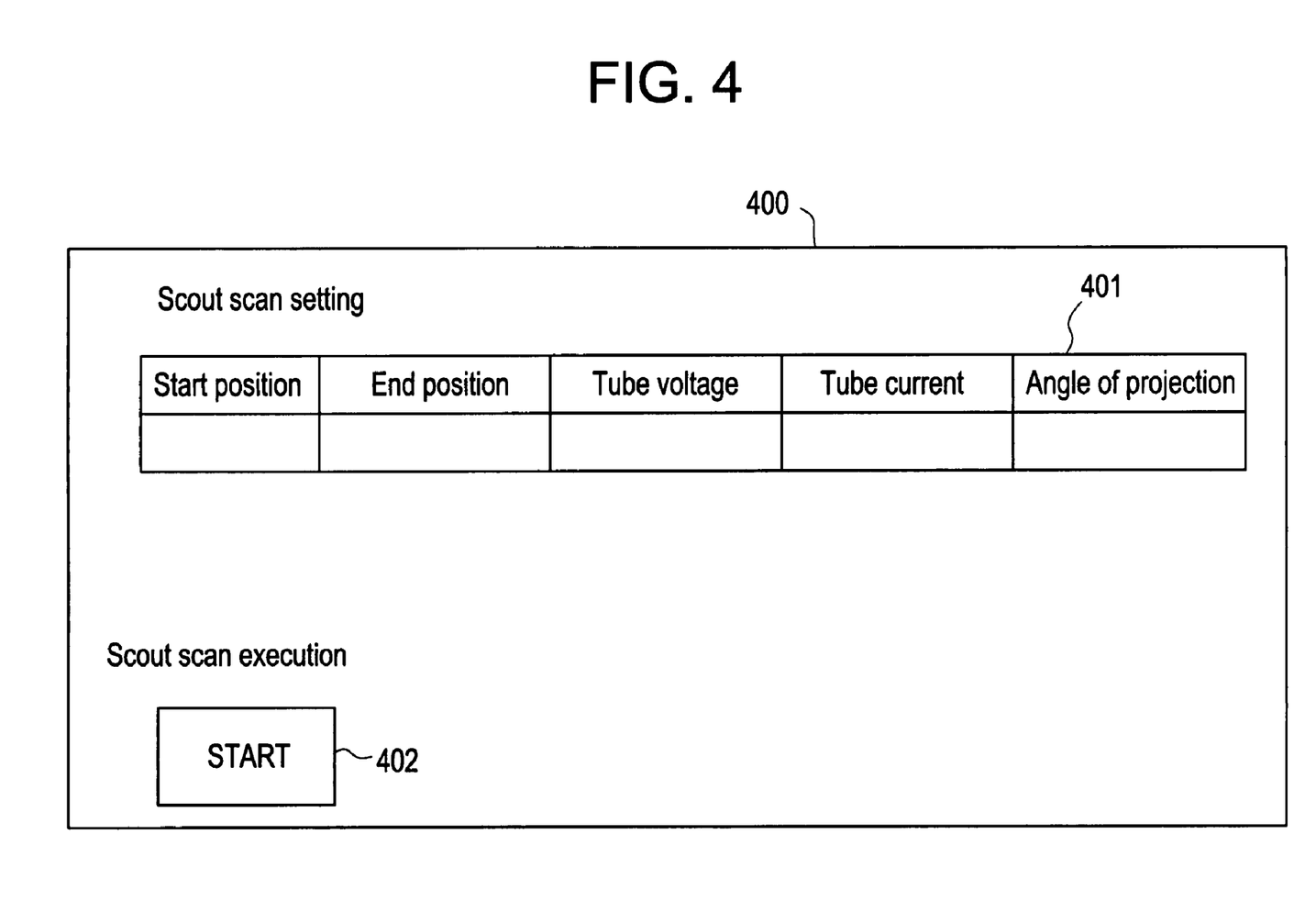
FIG. 4 shows an example of a screen image used to determine the conditions for a scout scan or to enter a scout scan execution command.

As illustrated, in a scout scan setting field, scout scan start and end positions, a tube voltage and a tube current for the X-ray tube 124, and an angle of projection 401 can be specified. In order to produce the aforesaid two kinds of scout images, 0° is specified for the angle of projection in the scout scan setting field. Thereafter, a start button 402 for executing a scout scan is pressed in order to execute the first scout scan. Thereafter, likewise, 90° is specified for the angle of projection in the scout scan setting field. Thereafter, the start button 402 is pressed in order to execute the second scout scan. Needless to say, the second scout scan may be executed first, and the mode in which the first and second scout scans are automatically successively executed may be employed. Moreover, a scout scan may be performed in order to construct one image.

Figure 5A:
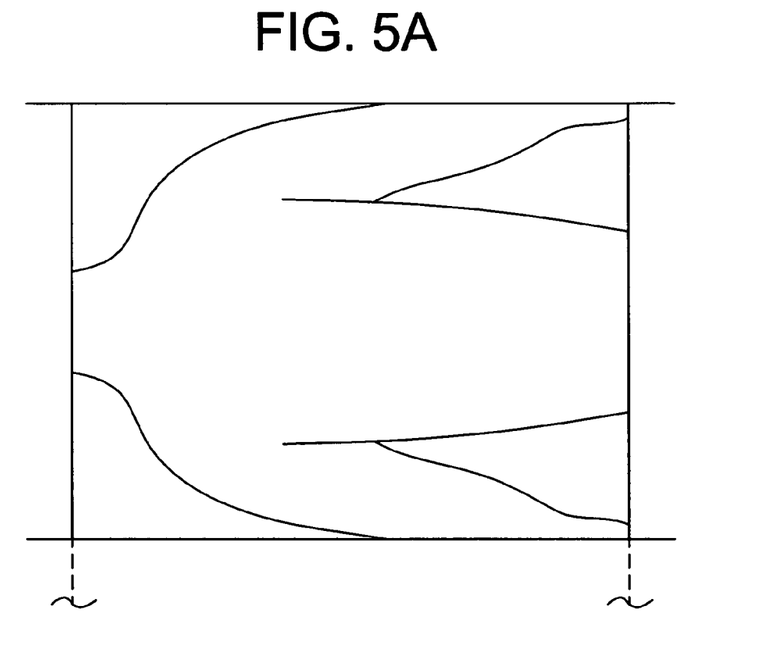
FIG. 5 shows an example of a scout image.

In response to a scout scan execution command, the gantry 120 executes a scout scan according to the contents of the plan (step S302). Projection data acquired during the scout scan is transferred to the operator console 100. Consequently, scout images representing the subject on the couch top 142 are constructed as shown in FIG. 5.

Figure 5B:
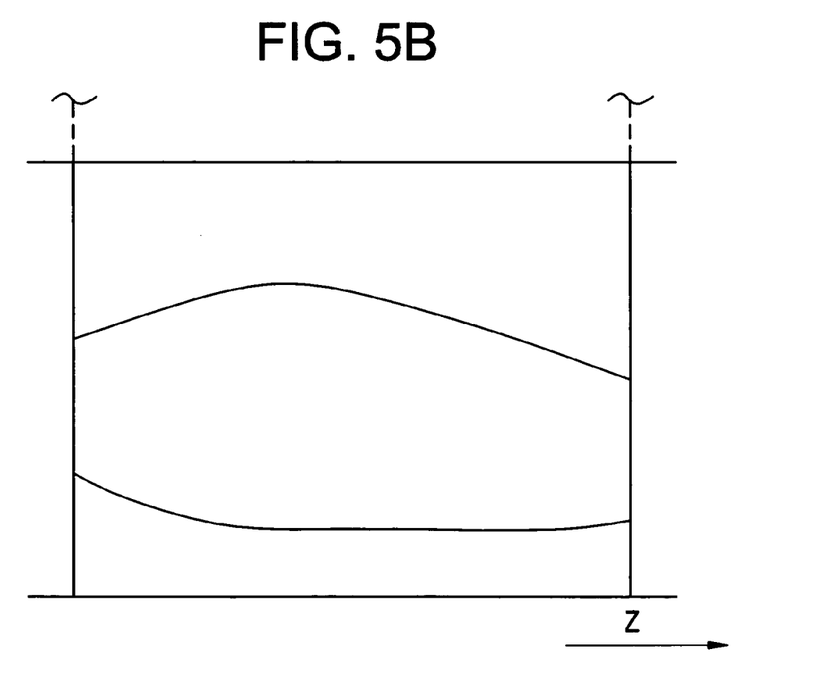

After the scout scan is completed, control is passed to step S202, and a scan is planned. The scan planning is performed through a scan planning screen image displayed on the CRT 102. Within the scan planning screen image, any of the two scout images (for example, scout image shown in FIG. 5(b)) is displayed. An operator proceeds with scan planning while viewing the scout image. The scanning plan will be detailed later.

After scan planning is completed, a scan is started (step S303) in response to a scan execution directive given by the operator (step S203). The scan is performed as described below. First, the position in the Z-axis direction of a patient is fixed, and an X-ray beam radiated from the X-ray tube 124 is irradiated to the patient (projection of X-rays). The X-ray detection unit 131 detects the transmitted X-rays. The detection of transmitted X-rays is repeated in a plurality of directions of views (for example, 1000 directions) over 360° while the X-ray tube 124 and X-ray detection unit 131 are rotated about the subject (that is, while an angle of projection is changed). This sequence is called a scan that is one unit. Detected transmitted X-rays are converted into digital values by the data acquisition unit 130, and transmitted as projection data to the operator console 100 via the DAS interface 136. A scanned position is shifted by a predetermined length in the Z-axis direction, and the next scan is performed. This scanning technique is called a conventional (axial scan) technique. Alternatively, a helical scan technique may be adopted so that projection data will be acquired while the scanned position is being shifted synchronously with a change in an angle of projection (namely, the X-ray tube 124 and X-ray detection unit 131 helically revolve about the patient).

Every after a scan is completed, the operator console 100 reconstructs an X-ray tomographic image on the basis of transferred projection data (step S204), and displays the image on the CRT 102 (step S205).

<Scout Image Display and Scan Planning>

Scout image display and scan planning of step S202 will be described below.

Figure 6:
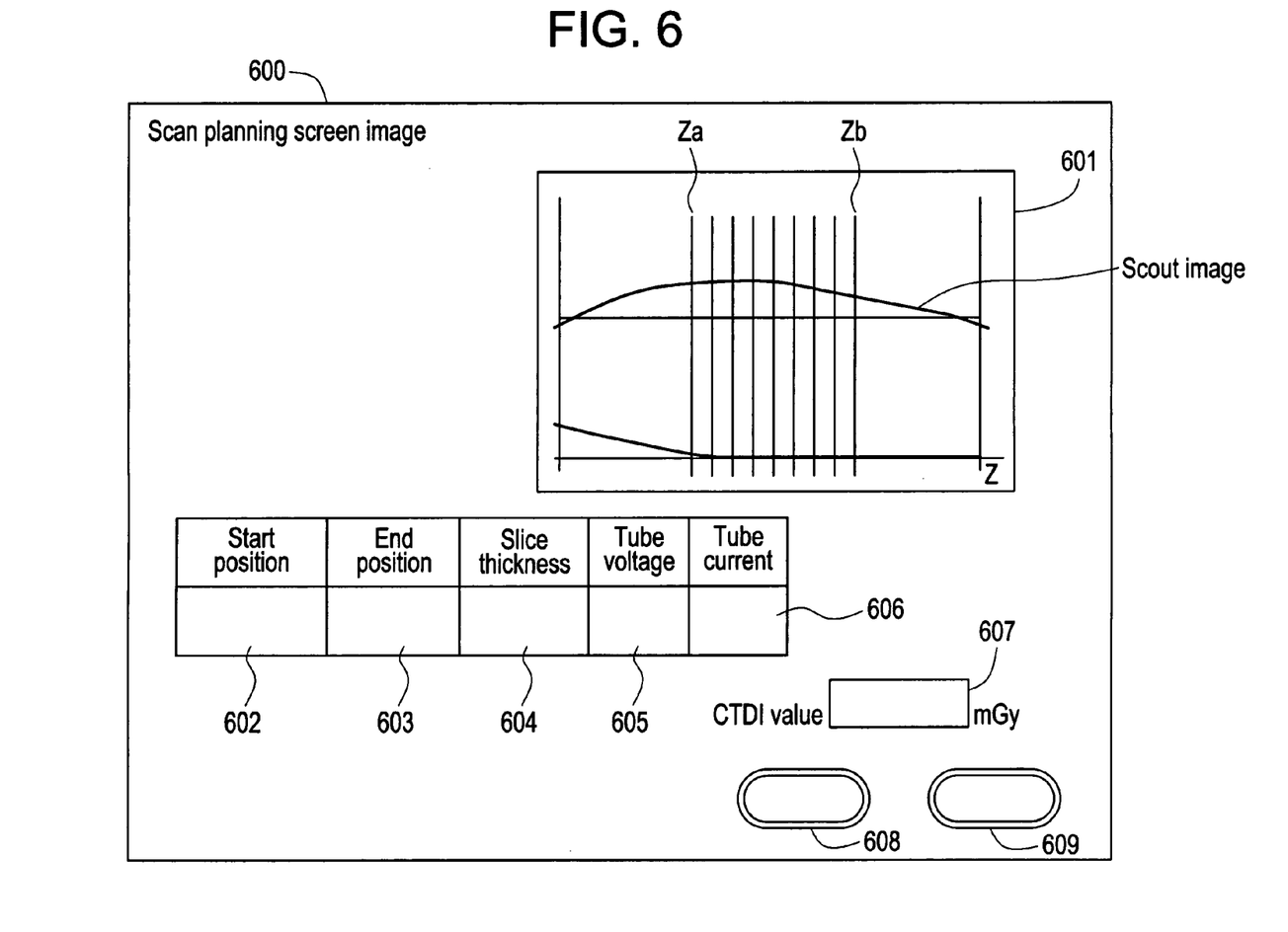
FIG. 6 shows an example of a scan planning screen image.

FIG. 6 shows an example of a scan planning screen image displayed on the CRT 102. Referring to FIG. 6, reference numeral 601 denotes an image area in which a scout image resulting from the scout scan performed at step S302 is displayed. A section 602 "start position" is a section in which a scan start position is entered relative to a predetermined reference position. Likewise, a section 603 "end position" is a section in which a scan end position is entered relative to a predetermined reference position. A section 604 "slice thickness" is a section in which a slice thickness determined for a scan is entered. A section 605 "tube voltage" is a section in which a tube voltage to be applied to the X-ray tube 124 is entered. A section 606 "tube current" is a section in which a tube current that flows through the X-ray tube 124 is entered. When values are entered in the section 602 "start position" and section 603 "end position," a line Za indicating the scan start position and a line Zb indicating the scan end position are displayed on the scout image in the image area 601. Thereafter, when a value is entered in the section 604 "slice thickness," lines indicating scanned positions are displayed within the range from the line Za to line Zb according to the entered values.

Reference numeral 607 denotes a CTDI value section. As described in relation to the related art, the CTDI value represents an estimated patient exposure which a patient receives during a scan and which is calculated based on the conditions for a scan (tube voltage 605 and tube current 606) determined through scan planning.

Reference numerals 608 and 609 denote a Retrieve Image History button and a Display Dose Distribution button. These buttons are included in a user interface required to execute image history retrieval, dose distribution creation, and dose distribution display (herein, a dose distribution refers to the distribution in the Z-axis direction of cumulative exposures). Referring to FIG. 7, FIG. 8, FIG. 9, and FIG. 10, the image history retrieval, dose distribution creation, and dose distribution display will be detailed below.

<Image History Retrieval and Dose Distribution Creation>

Figure 7:
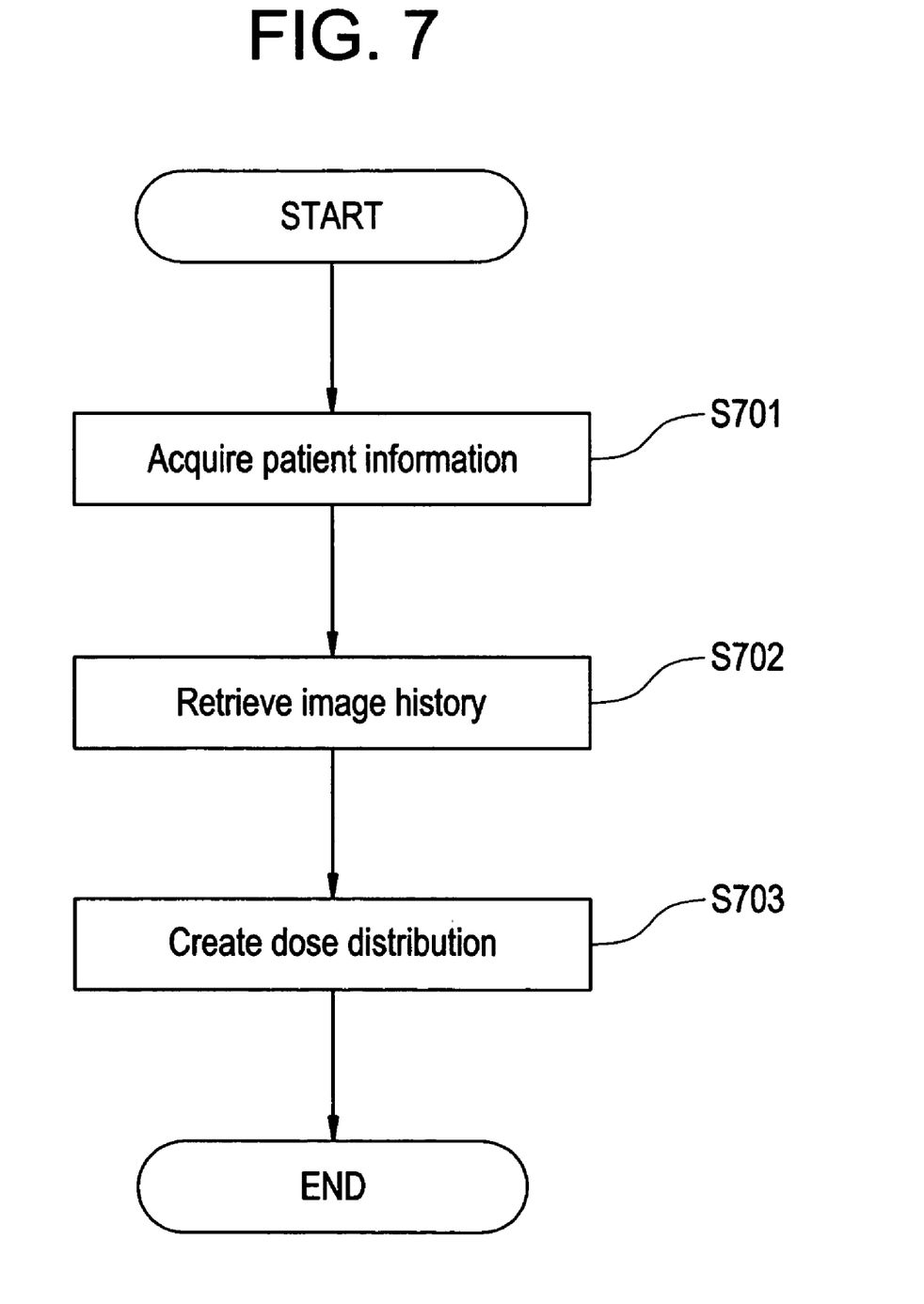
FIG. 7 is a flowchart describing a flow including image history retrieval and dose distribution creation and being employed in the X-ray CT system in accordance with the first embodiment of the present invention.

FIG. 7 is a flowchart describing a flow including image history retrieval and dose distribution creation. The process described in the flowchart is executed with a press of the Retrieve Image History button 608 shown in FIG. 6

First, at step S701, patient information is acquired. The patient information is detailed information on a patient registered in advance for a scan. For example, the patient information includes a patient identifier (ID), a patient name, a date of birth, and others.

At step S702, an image history is retrieved based on the patient information. According to the present embodiment, X-ray tomographic images stored in the HDD 108 are retrieved based on the patient ID. X-ray tomographic images bearing the patient ID and having been constructed over the past year are sampled. A retrieving method, a destination of retrieval, and a period of retrieval are not limited to the described ones. Moreover, an object of retrieval is not limited to X-ray tomographic images but may be radiographs. The destination of retrieval is not limited to the X-ray CT system but may include a database in a server. In this case, a dose distribution can be created more highly precisely.

Figure 8:
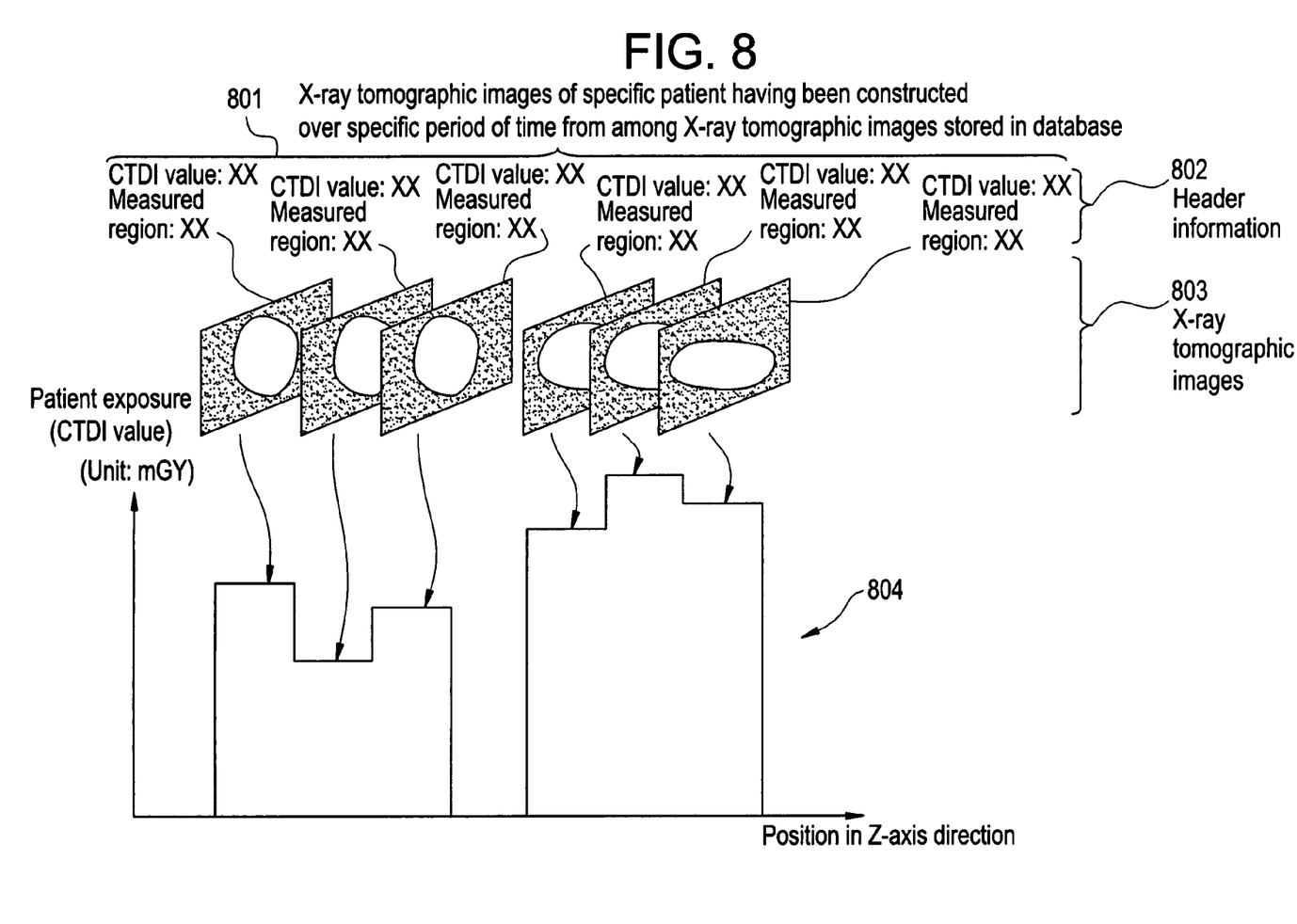
FIG. 8 shows the concepts of image history retrieval and dose distribution creation that are adopted for the X-ray CT system in accordance with the first embodiment of the present invention.

At step S703, a dose distribution is created based on sampled X-ray tomographic images. FIG. 8 outlines dose distribution creation. Referring to FIG. 8, reference numeral

801 denotes X-ray tomographic images having been constructed over the past year and being sampled based on a specific patient ID from among X-ray tomographic images stored in the HDD 108.

Each of the X-ray tomographic images 803 has header information 802 appended thereto. In order to create a dose distribution, a CTDI value and a sliced position in the Z-axis direction that are contained in the header information 802 are read. A cumulative value of CTDI values read from X-ray tomographic images sampled relative to each position in the Z-axis direction is plotted in order to create a dose distribution 804. In the example shown in FIG. 8, since one X-ray tomographic image is sampled relative to each position in the Z-axis direction, the read CTDI values are plotted as they are. If a plurality of X-ray tomographic images is sampled relative to the same position in the Z-axis direction, a cumulative value of CTDI values read from the X-ray tomographic images is plotted.

<Dose Distribution Display>

Figure 9:
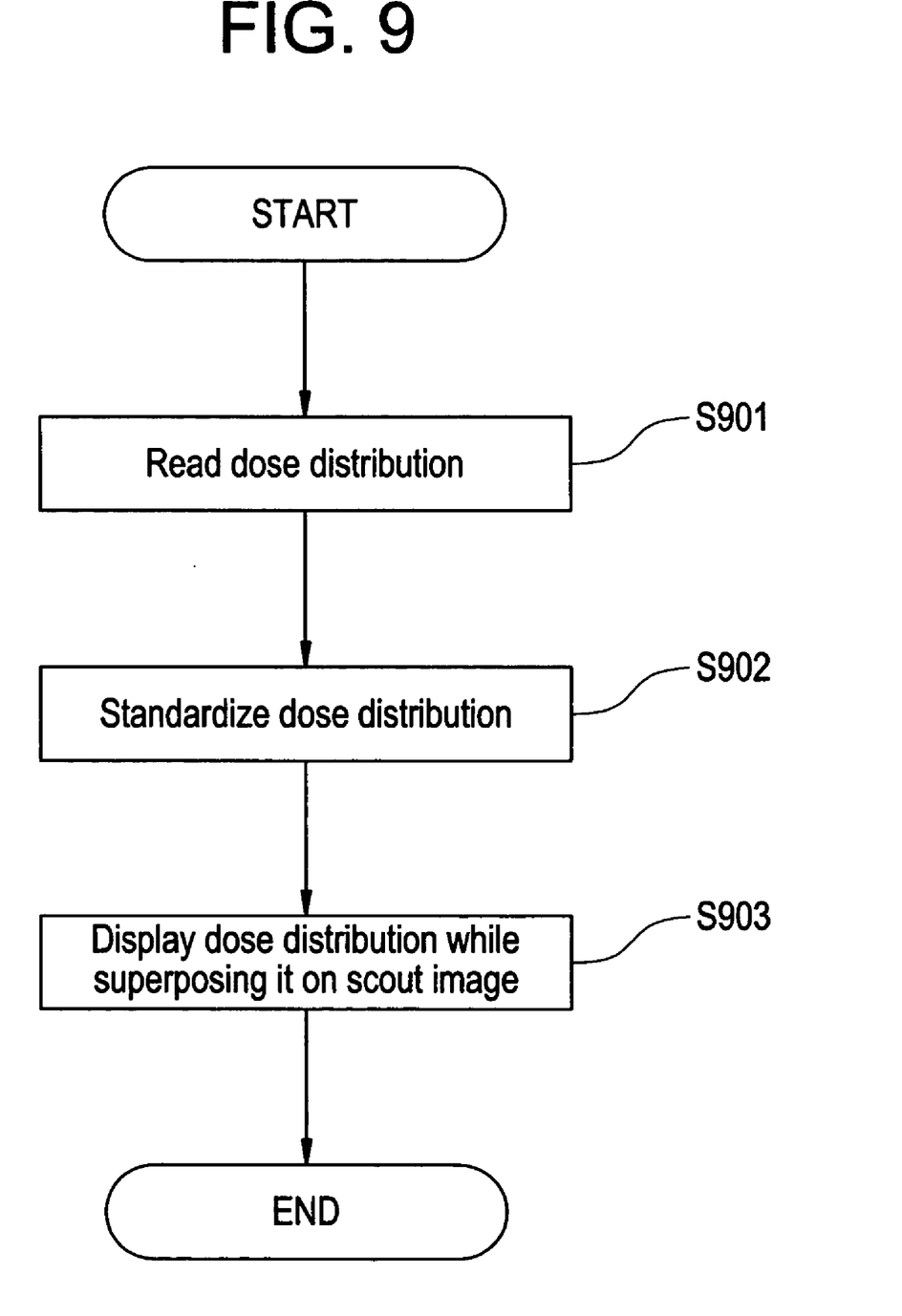
FIG. 9 is a flowchart describing the flow of dose distribution display employed in the X-ray CT system in accordance with the first embodiment of the present invention.

FIG. 9 is a flowchart describing the flow of dose distribution display. The dose distribution display is executed with a click made in the Display Dose Distribution button 609 shown in FIG. 6.

Figure 10:
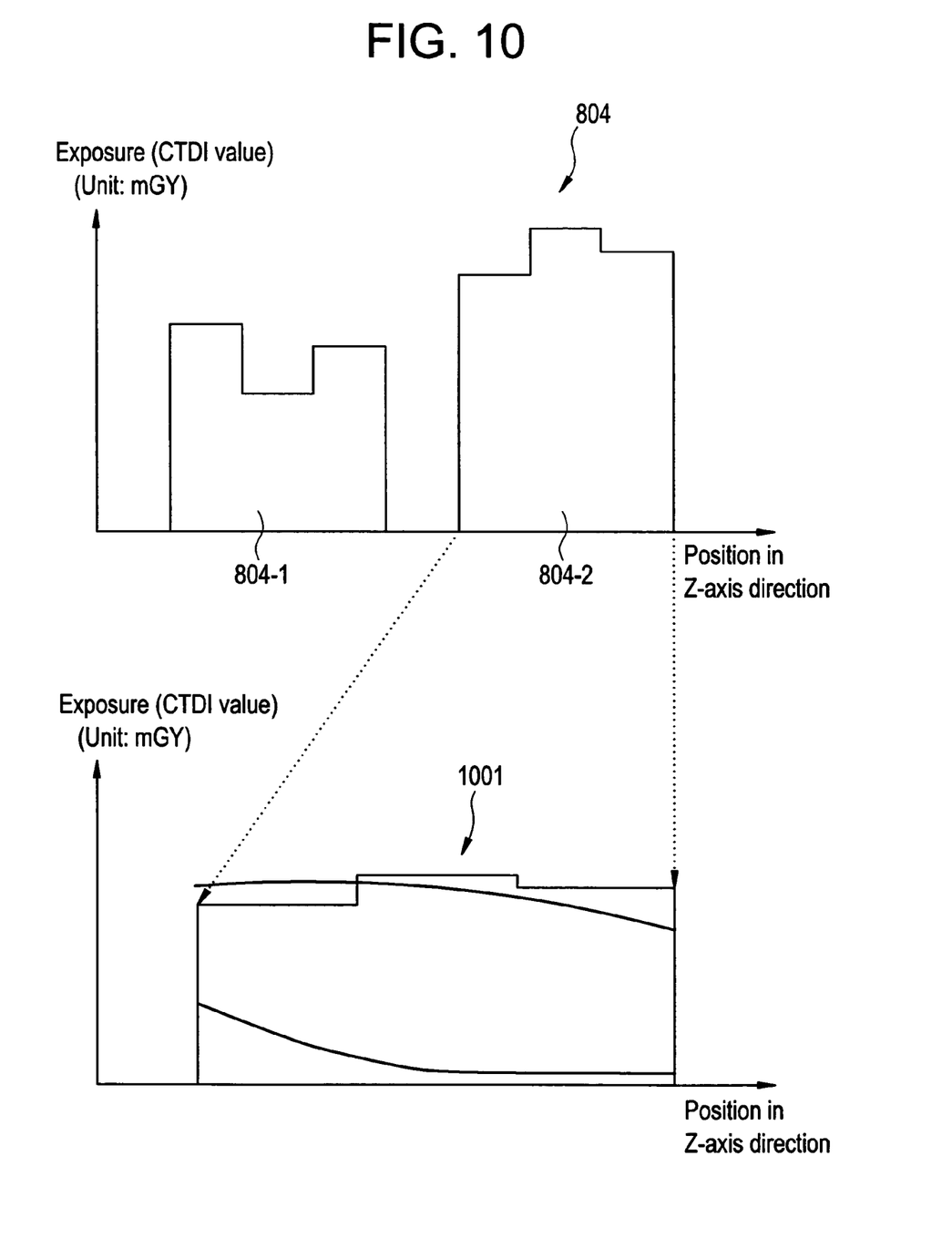
FIG. 10 shows the concept of dose distribution display adopted for the X-ray CT system in accordance with the first embodiment of the present invention.

At step S901, a created dose distribution is read. The read dose distribution is standardized at step S902. Referring to FIG. 10, the standardization (step S902) will be described.

As mentioned above, a dose distribution created as described in the flowchart of FIG. 7 is a graph indicating CTDI values appended to X-ray tomographic images that bear a specific patient ID and have been constructed over the past year. In contrast, a scout image representing a region scanned during a scout scan is displayed in the scan planning screen image 600.

The scales in the Z-axis direction on the scout image are read, and the scales in the Z-axis direction on the dose distribution are standardized to conform to the read scales so that the scales on the dose distribution will match those on the scout image. FIG. 10 is a conceptual diagram concerning the standardization. The graph 804 represents the dose distribution created as described in the flowchart of FIG. 7. A graph 1001 represents a standardized dose distribution.

As shown in FIG. 10, a dose distribution 804-2 associated with a scout image 601 representing a patient's chest is sampled, and deformed so that the scales in the Z-axis direction will match those on the scout image. This results in the dose distribution 1001.

Figure 11:
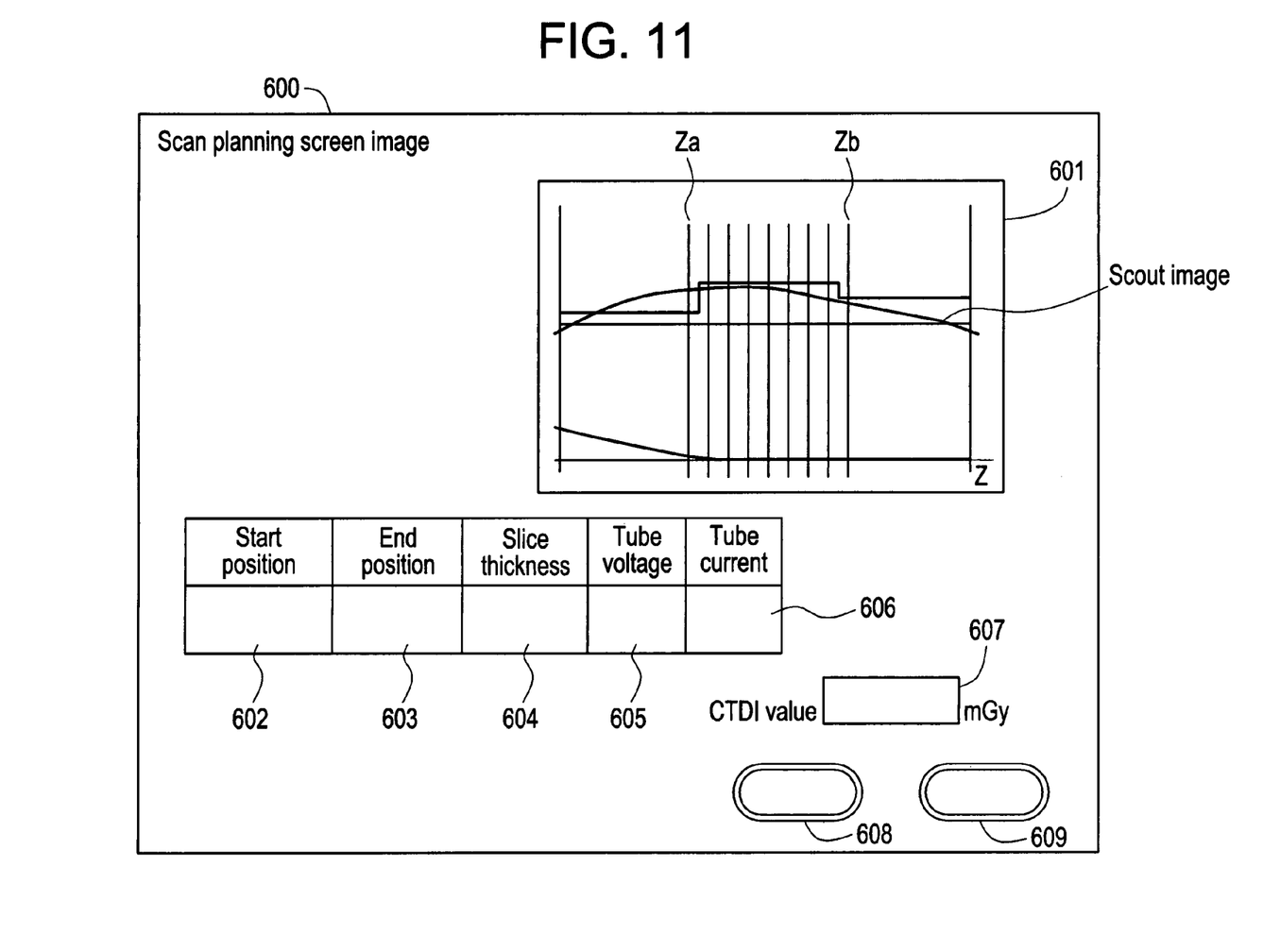
FIG. 11 shows an example of a scan planning screen image within which a dose distribution is displayed.

FIG. 11 shows an example of a scan planning screen image with the Display Dose Distribution button 609 pressed. As illustrated, a distribution of doses to which a patient has been exposed over the past year is standardized in the Z-axis direction and displayed together with a scout image at step (S903). An operator can therefore plan a scan while viewing the display.

Namely, in consideration of a cumulative patient exposure of past patient exposures, a case where a patient exposure should be suppressed despite degradation in image quality can be discriminated from a case where a patient exposure may be raised in order to improve image quality.

As apparent from the above description, according to the present embodiment, a scan can be planned easily in consideration of past patient exposures.

[Second Embodiment]

According to the first embodiment, a distribution of doses to which a patient has been exposed over the past year is displayed in the scan planning screen image. The present invention is not limited to this mode. A CTDI value 607 that can be calculated based on the conditions for a scan determined in the scan planning screen image (CTDI value for a scan to be performed this time) may be added to a value indicated by the dose distribution. In this case, an operator can readily recognize the sum total of past patient exposures and a patient exposure caused by this scan. Moreover, the limit of a patient exposure may also be indicated. In this case, an exposure of what region should be reduced can be recognized. This will prove helpful.

Moreover, a reference value for a cumulative patient exposure may also be indicated. Consequently, whether the determined conditions for a scan are appropriate can be recognized at sight.

[Other Embodiments]

In the aforesaid embodiments, the X-ray CT system is almost always controlled at the operator console 100. The configuration of the operator console 100 can be realized with a general-purpose information processing unit (workstation or personal computer). Software may be installed in the information processing unit in order to realize the operator console 100. Namely, a storage medium in which a software program realizing the constituent features of the aforesaid embodiment is stored may be included in an X-ray CT system. A computer (or a CPU or MPU) included in the X-ray CT system may read the program from the storage medium and run it. Thus, the present invention may be implemented.

In this case, the program read from the storage medium realizes the constituent features of the aforesaid embodiment, and the storage medium in which the program is stored is included in the present invention.

As the storage medium for use in providing the program, for example, a floppy® disk, a hard disk, an optical disk, a magneto-optical disk, a CD-ROM, a CD-R, a magnetic tape, a nonvolatile memory card, or a ROM may be adopted.

When the computer runs the read program, the constituent features of the aforesaid embodiment are implemented. Moreover, based on a directive given by the program, an operating system (OS) residing in the computer may perform part or the whole of actual processing. Due to the processing, the aforesaid constituent features of the aforesaid embodiment may be realized.

Furthermore, the program read from the storage medium is written in a memory included in a function expansion board inserted in the computer or a function expansion unit connected to the computer. Thereafter, a CPU or the like included in the function expansion board or unit may perform part or the whole of actual processing in response to a directive given by the program. Owing to the processing, the constituent features of the embodiment may be realized.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An X-ray CT system for performing a scan so as to irradiate X-rays, which are generated from an X-ray tube, to a subject from a plurality of directions, and for reconstructing tomographic images of the subject, comprising:
    a sampling device for sampling information on a first set of exposures said subject has received during a scan performed for constructing tomographic images, which is appended to each of the reconstructed tomographic images, on the basis of identification information with which said subject is identified;

a creating device for creating an exposure distribution of the exposures, which are calculated relative to an axis orthogonal to the scanning directions, on the basis of the sampled information on the exposures, wherein the axis includes a first position and a second position, wherein the exposures include a first exposure of the subject to x-rays and a second exposure of the subject to x-rays, and wherein the first exposure is calculated at the first position and the second exposure is calculated at the second position; and a display device on which said exposure distribution is displayed.

2. An X-ray CT system according to claim 1, wherein on said display device, said exposure distribution is displayed while being superposed on a scanogram that is produced by transporting said subject with said X-ray tube fixed at a predetermined position.

3. An X-ray CT system according to claim 1, wherein said display device is configured to display a scanogram, wherein on said display device, said exposure distribution is displayed while being superposed so that the positions in said scanogram and the positions indicated in said exposure distribution agree with each other relative to the axis orthogonal to the scanning directions.

4. An X-ray CT system according to claim 1, wherein said identification information contains any of an identifier (ID) assigned to a subject and a subject name.

5. An X-ray CT system according to claim 1, wherein based on the identification information with which said subject is identified, said sampling device samples exposure information appended to each of tomographic images reconstructed over a predetermined period of time.

6. An X-ray CT system according to claim 1, wherein when said sampling device samples a plurality of pieces of information on a second set of exposures to the same position on the axis orthogonal to the scanning directions, said creating device creates an exposure distribution using the cumulative information of the pieces of information on the plurality of exposures within the second set.

7. An X-ray CT system according to claim 1, wherein a permissible value of an exposure said subject receives over the predetermined period of time is indicated.

8. An X-ray CT system according to claim 1, wherein the first exposure is of a different value than the second exposure.

9. An X-ray CT system for performing a scan so as to irradiate X-rays, which are generated from an X-ray tube, to a subject from a plurality of directions, and for reconstructing tomographic images of the subject, comprising:

a sampling device for sampling information on an exposure said subject has received during a scan performed for constructing tomographic images, which is appended to each of the reconstructed tomographic images, on the basis of identification information with which said subject is identified;

a creating device for creating an exposure distribution of exposures, which are calculated relative to an axis orthogonal to the scanning directions, on the basis of the sampled information on the exposure; and a display device on which said exposure distribution is displayed, wherein on said display device, an exposure said subject receives when scanned is indicated while being added to a value indicated by said exposure distribution.

10. An X-ray CT system for performing a scan so as to irradiate X-rays, which are generated from an X-ray tube, to a subject from a plurality of directions, and for reconstructing tomographic images of the subject, comprising:

a sampling device for sampling information on an exposure said subject has received during a scan performed for constructing tomographic images, which is appended to each of the reconstructed tomographic images, on the basis of identification information with which said subject is identified;

a creating device for creating an exposure distribution of exposures, which are calculated relative to an axis orthogonal to the scanning directions, on the basis of the sampled information on the exposure; and a display device on which said exposure distribution is displayed, wherein on said display device, an exposure said subject receives when scanned is indicated during scan planning while being added to a value indicated by said exposure distribution.

11. An information processing method to be implemented in an X-ray CT system that performs a scan so as to irradiate X-rays, which are generated from an X-ray tube, to a subject from a plurality of directions, and reconstructs tomographic images of said subject, said information processing method comprising:

a sampling step of sampling information on a first set of exposures said subject has received during a scan performed for reconstructing tomographic images, which is appended to each of the reconstructed tomographic images, on the basis of identification information with which said subject is identified;

a creating step of creating an exposure distribution of the exposures, which are calculated relative to an axis orthogonal to the scanning directions, on the basis of the sampled information on the exposures, wherein the axis includes a first position and a second position, wherein the exposures include a first exposure of the subject to x-rays and a second exposure of the subject to x-rays, and wherein the first exposure is calculated at the first position and the second exposure is calculated at the second position; and a display step of displaying the exposure distribution.

12. An information processing method according to claim 11, wherein at said display step, said exposure distribution is displayed while being superposed on a scanogram that is produced by transporting a subject with said X-ray tube fixed at a predetermined position.

13. An information processing method according to claim 12, wherein at said display step, said exposure distribution is displayed while being superposed so that a plurality of positions in a scanogram and the positions indicated in said exposure distribution agree with each other relative to the axis orthogonal to the scanning directions.

14. An information processing method according to claim 11, wherein said identification information contains any of an identifier (ID) assigned to a subject and a subject name.

15. An information processing method according to claim 11, wherein at said sampling step, exposure information appended to each of the tomographic images reconstructed over a predetermined period of time is sampled based on the identification information with which said subject is identified.

16. An information processing method according to claim 11, wherein at said creating step, when a plurality of pieces of information on a second set of exposures to the same position on the axis orthogonal to the scanning directions are sampled at said sampling step, said exposure distribution is created using cumulative information of the pieces of information on the plurality of exposures within the second set.

17. An information processing method according to claim 11, wherein at said display step, a permissible value of an exposure said subject receives over the predetermined period of time is indicated.

18. An information processing method to be implemented in an X-ray CT system that performs a scan so as to irradiate X-rays, which are generated from an X-ray tube, to a subject from a plurality of directions, and reconstructs tomographic images of said subject, said information processing method comprising:
   a sampling step of sampling information on an exposure said subject has received during a scan performed for reconstructing tomographic images, which is appended to each of the reconstructed tomographic images, on the basis of identification information with which said subject is identified;
   a creating step of creating an exposure distribution of exposures, which are calculated relative to an axis orthogonal to the scanning directions, on the basis of the sampled information on the exposure; and
   a display step of displaying the exposure distribution, wherein at said display step, an exposure said subject receives when scanned is indicated while being added to a value indicated by said exposure distribution.

19. An information processing method to be implemented in an X-ray CT system that performs a scan so as to irradiate X-rays, which are generated from an X-ray tube, to a subject from a plurality of directions, and reconstructs tomographic images of said subject, said information processing method comprising:
   a sampling step of sampling information on an exposure said subject has received during a scan performed for reconstructing tomographic images, which is appended to each of the reconstructed tomographic images, on the basis of identification information with which said subject is identified;
   a creating step of creating an exposure distribution of exposures, which are calculated relative to an axis orthogonal to the scanning directions, on the basis of the sampled information on the exposure; and
   a display step of displaying the exposure distribution, wherein at said display step, an exposure said subject receives when scanned is indicated during scan planning while being added to a value indicated by said exposure distribution.

20. A computer program embodied on a computer readable medium for controlling an X-ray CT system that performs a scan so as to irradiate X-rays, which are generated from an X-ray tube, to a subject from a plurality of directions, and reconstructs tomographic images of said subject, said program configured to:
   sample information on a first set of exposures the subject has received during a scan performed for reconstructing tomographic images, which is appended to each of the reconstructed tomographic images, on the basis of identification information with which the subject is identified;
   create an exposure distribution of the exposures, which are calculated relative to an axis orthogonal to the scanning directions, on the basis of the sampled information on the exposures, wherein the axis includes a first position and a second position, wherein the exposures include a first exposure of the subject to x-rays and a second exposure of the subject to x-rays, and wherein the first exposure is calculated at the first position and the second exposure is calculated at the second position; and
   display the exposure distribution.

* * * * *